(12) United States Patent
Haidukewych

(10) Patent No.: US 11,141,202 B1
(45) Date of Patent: Oct. 12, 2021

(54) METHOD TO STABILIZE AN INTRAMEDULLARY NAIL

(71) Applicant: George J. Haidukewych, Orlando, FL (US)

(72) Inventor: George J. Haidukewych, Orlando, FL (US)

( * ) Notice: Subject to any disclaimer, the term of this patent is extended or adjusted under 35 U.S.C. 154(b) by 138 days.

(21) Appl. No.: 16/501,036

(22) Filed: Feb. 12, 2019

(51) Int. Cl.
    *A61B 17/72* (2006.01)
    *A61B 17/17* (2006.01)
    *A61B 17/74* (2006.01)
    *A61B 17/86* (2006.01)

(52) U.S. Cl.
    CPC ...... *A61B 17/7233* (2013.01); *A61B 17/1717* (2013.01); *A61B 17/1725* (2013.01); *A61B 17/1753* (2013.01); *A61B 17/8625* (2013.01); *A61B 17/744* (2013.01)

(58) Field of Classification Search
    CPC .. A61B 17/72–7291; A61B 17/74–748; A61B 17/1717; A61B 17/1753; A61B 17/1725; A61B 17/8625
    See application file for complete search history.

(56) References Cited

U.S. PATENT DOCUMENTS

| | | | | |
|---|---|---|---|---|
| 5,176,681 A | * | 1/1993 | Lawes | A61B 17/744 606/64 |
| 5,374,235 A | * | 12/1994 | Ahrens | A61B 17/72 606/101 |
| 6,120,504 A | * | 9/2000 | Brumback | A61B 17/72 606/62 |
| 9,622,798 B2 | * | 4/2017 | Merrell | A61B 17/7225 |
| 2003/0083661 A1 | * | 5/2003 | Orbay | A61B 17/8061 606/62 |
| 2007/0219636 A1 | * | 9/2007 | Thakkar | A61B 17/744 623/18.11 |
| 2008/0021474 A1 | * | 1/2008 | Bonutti | A61B 17/866 606/64 |
| 2009/0062797 A1 | * | 3/2009 | Huebner | A61B 17/7225 606/62 |

(Continued)

*Primary Examiner* — Nicholas J Plionis
(74) *Attorney, Agent, or Firm* — Arthur W. Fisher, III

(57) ABSTRACT

A method to secure and stabilize an intramedullary nail in the medullary canal of a fractured hip including the steps of positioning the intramedullary nail within the medullary canal, positioning an alignment tool including a plurality of alignment bores on the intramedullary nail to align drill bits to drill holes or channels in the femur neck, femur cortex and upper and lower portions of the intramedullary nail, threading a femur neck screw through the corresponding alignment bore into a channel in the femur neck, through the hole in the upper portion of the intramedullary nail and into the head, threading a locking screw through the corresponding alignment bore and a hole in the proximal cortex and channel in the lower portion of the intramedullary nail and into the distal cortex, threading a stabilizer member through the corresponding alignment bore until the distal end portion engages the proximal surface of the intramedullary nail to limit lateral movement of the intramedullary nail thereby stabilizing the intramedullary nail in the medullary canal and removing the alignment tool from the upper portion of the intramedullary nail.

5 Claims, 8 Drawing Sheets

(56) References Cited

U.S. PATENT DOCUMENTS

| | | | | |
|---|---|---|---|---|
| 2010/0211073 A1* | 8/2010 | Merrell | ............. | A61B 17/1739 |
| | | | | 606/62 |
| 2012/0022534 A1* | 1/2012 | Orbay | ................ | A61B 17/7241 |
| | | | | 606/62 |
| 2015/0320461 A1* | 11/2015 | Ehmke | ............... | A61B 17/8685 |
| | | | | 606/67 |

* cited by examiner

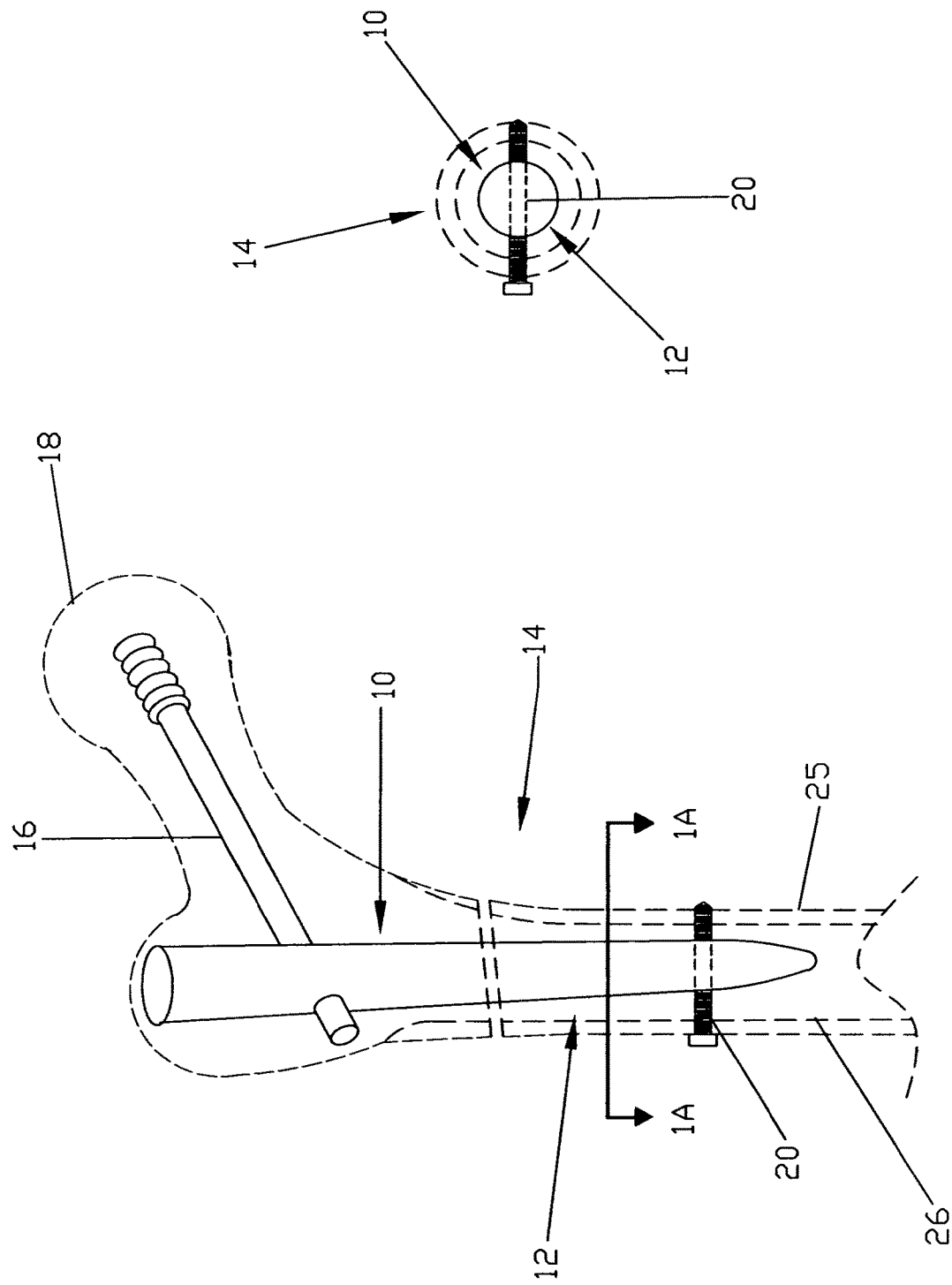

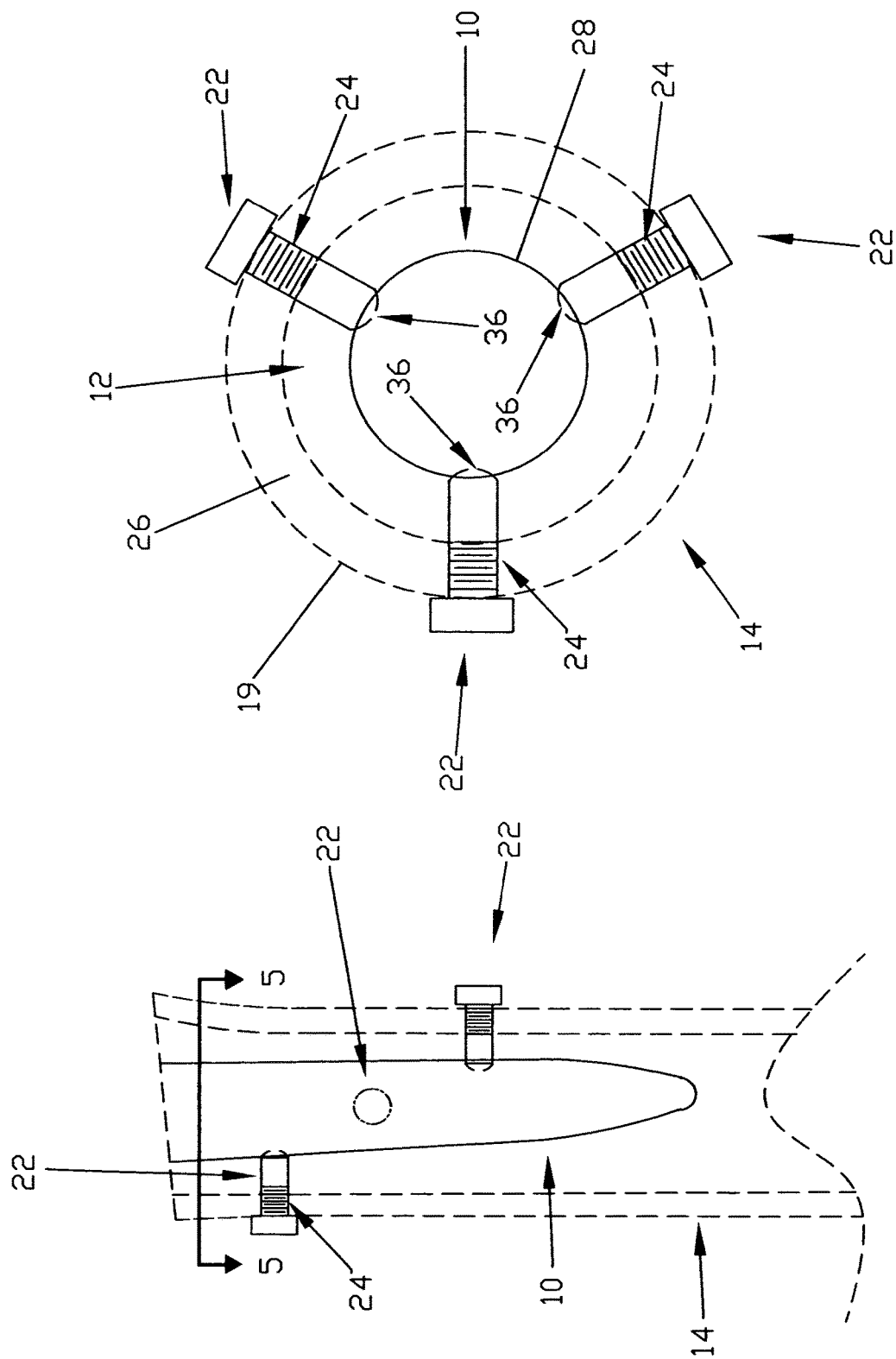

METHOD TO STABILIZE AN INTRAMEDULLARY NAIL

BACKGROUND OF THE INVENTION

Field of the Invention

A method to secure and stabilize an intramedullary nail implanted in a medullary canal of a fractured hip.

Description of the Prior Art

Intramedullary fracture fixation devices generally comprise an intramedullary rod or nail having an opening to receive a femoral neck screw such as a lag screw. The intramedullary rod or nail is fitted or placed in the intramedullary canal of the femur and the femur neck screw is passed through an opening in the intramedullary rod or nail through the neck of the femur and into the head to produce tension in the femur neck screw to draw the head and neck of the femur together.

To assist in the positioning and securing such an intramedullary rod or nail in place, a jig or alignment tool may be used to properly position fasteners and other structural members during the implant procedure. Specifically, the jig or alignment tool may be clamped to the upper end of the intramedullary rod or nail to provide an alignment guide to drill a femur neck screw hole and channel and to drill a hole at the distal end of the femur to locate a lock screw in the lower end of the intramedullary rod or nail.

Numerous examples of intramedullary nails used to treat hip fractures are found in the prior art. In addition, various methods of implanting intramedullary nails using alignment jigs or fixtures are found in the prior art. Examples of the prior art are herein identified.

U.S. Pat. No. 8,734,448 ('448) discloses a proximal femur fracture implant assembly comprising a targeting device and intramedullary nail having a plurality of proximal holes directed toward the head and neck of the femur. FIG. 30 depicts a plurality of cortical screws 85 that engages the side or surface of the intramedullary nail which, in effect, act or serve as "bumpers."

2017/0189092 ('092 shows a method of stabilizing a bone fracture by positioning an elongate rod or nail in the medullary canal of a fractured bone, securing a bone plate against the exterior of the fractured bone and stabilizing the elongate rod or nail within the medullary canal with at least one fastener welded in an indention or recess formed in the surface of the elongate rod or nail as shown in FIGS. 23D and 266 that, in effect, act as "bumpers."

US 2016/0346025 relates to a method of fastening and stabilizing implants that may include a fastener having a deformable distal end to fill the gap between the implant and body tissue as shown in FIG. 30.

'092 and '448 describe the use of screws or fasteners configured to engage the outer surface of an intramedullary nail to stabilize the position of the intramedullary nail within the medullary canal. In addition, the distal end of each fastener of '092 is disposed with an indentation or recess.

The following are additional examples of the prior art: U.S. Pat. Nos. 3,433,220, 4,622,959, 5,176,681, 5,374,235, 5,743,908, 5,766,174, 6,126,661, U.S. Pat. Nos. 6,387,098, 6,409,768, 7,588,577, 7,727,264, 7,780,664, 8,114,079 and 9,907,592.

While some of the prior art may contain some similarities relating to the present invention, none of them teach, suggested or include all of the advantages and unique features of the invention disclosed hereafter.

SUMMARY OF THE INVENTION

The present invention relates to a method to secure and stabilize a intramedullary nail implanted in the medullary canal of a fractured femur to maintain alignment of the femur.

The upper portion of the intramedullary nail is secured in place within the intramedullary canal by threading a femur neck screw into the upper portion of the femur through the intramedullary nail and into the head. The lower or distal portion of the intramedullary nail is secured within the intramedullary canal by threading a locking screw through the lower portion of the femur and through the intramedullary nail.

The femur neck screw extends through a channel formed in the femur and channel or hole formed through the upper portion intramedullary nail and into the head.

The locking screw extends through a hole formed through the proximal cortex of the femur, through a channel or hole formed through the lower portion of the intramedullary nail and into the distal cortex of the femur.

In addition, at least one stabilizer member extends through a hole formed through the proximal cortex of the femur to engage the surface of the intramedullary nail.

The stabilizer member comprises a head having a shaft extending outwardly therefrom terminating in an outer end to engage the intramedullary nail.

An alignment tool is used to locate the correct positions or locations of the femur neck screw, stabilizer member and lower lock screw along the intramedullary nail.

The alignment tool includes a femur neck screw alignment bore, at least one stabilizer alignment bore and a locking screw alignment bore.

The alignment bores provide for the proper relative longitudinal spacing of the femur neck screw, stabilizer member(s) and locking screw along the length of the intermedullary nail.

One embodiment of the method of the present invention for securing and stabilizing the intramedullary nail to be implanted in the medullary canal comprises the steps of:

preparing the medullary canal to receive an intramedullary nail, positioning the intramedullary nail in the medullary canal, positioning an alignment tool including a femur neck screw alignment bore, a stabilizer member alignment bore and a locking screw alignment bore on the upper end portion of the intramedullary nail, aligning a drill bit through the femur neck screw alignment bore and drilling a channel in the femur and a channel or hole through the upper portion of the intramedullary nail and into the head, securing the upper portion of the intramedullary nail within the upper portion of the intramedullary canal by threading a femur neck screw through the femur channel and through the intramedullary channel or hole and into the head, aligning a drill bit through the locking screw alignment bore and drilling a hole through the proximal cortex and a channel or hole through the distal portion of the intramedullary nail, securing the lower portion of the intramedullary nail within the intramedullary canal by threading a locking screw through the hole formed in proximal cortex and the channel or hole formed in the lower portion of the intramedullary nail and into the distal cortex, aligning a drill bit through the stabilizer member alignment bore and drilling a hole through the proximal cortex of the femur, inserting a stabilizer member through the stabilizer alignment bore and threading the stabilizer member into the hole until the outer end portion of the stabilizer member engages the intramedullary nail to stabilize the intramedullary nail from lateral movement, and removing the alignment tool from the upper end portion of the intramedullary nail.

This summary is not intended to describe essential features of the claimed subject matter nor is it intended to limit the scope of the claimed subject matter. To the contrary, this Summary merely outlines various concepts and features that are developed in the Detailed Description.

BRIEF DESCRIPTION OF THE DRAWINGS

For a fuller understanding of the nature and object of the invention, reference should be had to the following detailed description taken in connection with the accompanying drawings in which:

FIG. 1 is a view of an intramedullary nail implanted in a fractured femur.

FIG. 1A is a top cross-sectional view of the intramedullary nail implanted in the fractured femur taken across line 1A-1A of FIG. 1.

FIG. 4 is a partial view of an intramedullary nail implanted in a fractured femur and the stabilizer members of the present invention.

FIG. 5 is a top cross-sectional view of the intramedullary nail implanted in a fractured femur and the stabilizer members of the present invention taken along line 5-5 of FIG. 4.

Similar reference characters refer to similar parts throughout the several views of the drawings.

DETAILED DESCRIPTION OF THE INVENTION

Figures 2, 2A:
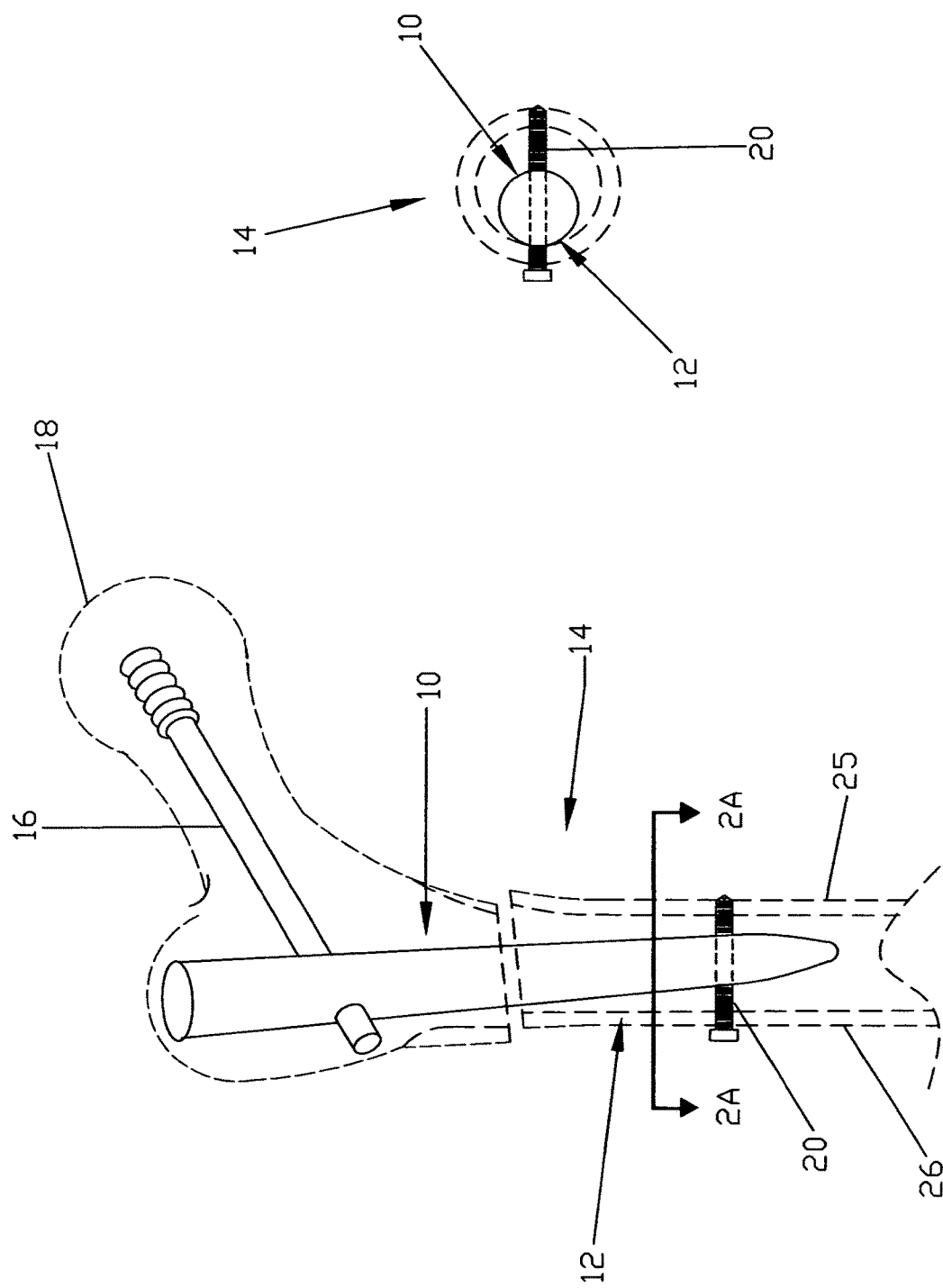
FIG. 2 is a view of an intramedullary nail implanted in a femur that has been misaligned due to shifting.
FIG. 2A is a top cross-sectional view of the intramedullary nail implanted in the fractured femur that has become misaligned due to shifting taken along line 2A-2A of FIG. 2.

FIGS. 1 and 1A depict an intramedullary nail generally indicated as 10 implanted in a medullary canal 12 of a fractured femur generally indicated as 14. The proximal portion of the intramedullary nail 10 is secured in place within the upper portion of intramedullary canal 10 by threading a femur neck screw 16 through the upper portion of the femur 14 and into the head 18. The distal portion of the intramedullary nail 10 is secured within the lower portion of the intramedullary canal 12 by threading a lower screw 20 through the lower portion of the femur 14.

Over time, the lower portion of the femur 14 may shift relative to the upper portion of the femur 14 misaligning the entire femur 14 as shown in FIGS. 2 and 2A.

If the femur remains misaligned as the femur 14 heals, the femur 14 becomes misaligned permanently. As a result, additional surgery may be dictated to realign the femur 14.

As described herein, the present invention relates to a method to secure and stabilize the intramedullary nail 10 implanted in the medullary canal 12 of a fractured femur 14 to maintain alignment.

Figure 3:
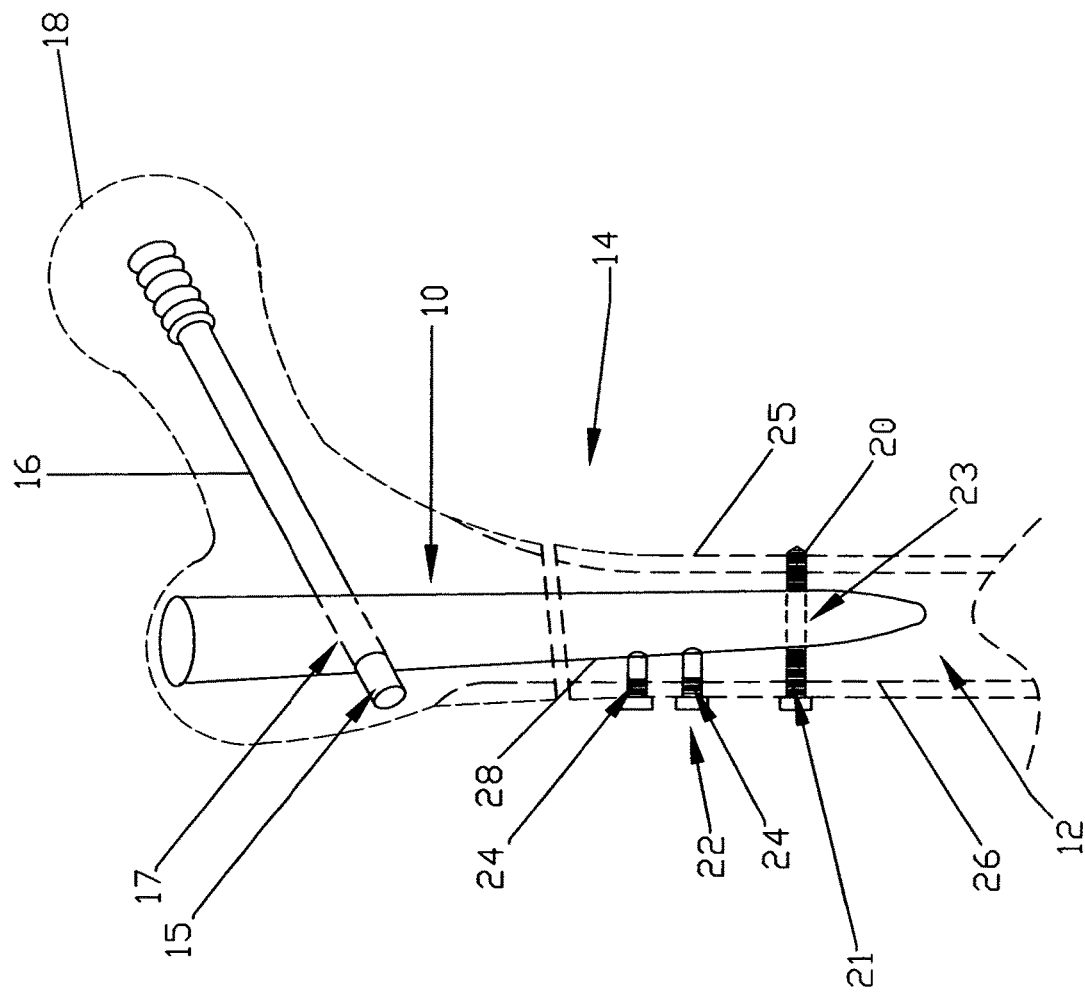
FIG. 3 is a view of an intramedullary nail implanted in a fractured femur and the stabilizer members of the present invention.

FIG. 3 depicts a intramedullary nail 10 implanted in a medullary canal 12 of a fractured femur 14 using the method of the present invention. The upper or proximal portion of the intramedullary nail 10 is secured in place within the intramedullary canal 10 by threading a femur neck screw 16 into the upper portion of the femur 14 and into the head 18. The lower or distal portion of the intramedullary nail 10 is secured within the intramedullary canal 12 by threading a locking screw 20 through the lower portion of the femur 14.

In particular, as shown in FIG. 3, the femur neck screw 16 extends through a channel 15 formed in the femur 14 and a nail channel or hole 17 formed through the upper portion intramedullary nail 10 and into the head 18.

As shown in FIG. 3, the locking screw 20 extends through a hole 21 formed through the proximal cortex 26 of the femur 14, through a channel or hole 23 formed through the lower portion of the intramedullary nail 10 and into the distal cortex 25 of the femur 14.

In addition, a pair of stabilizer members each generally indicated as 22 extend through corresponding holes 24 formed through the proximal cortex 26 of the femur 14 to engage the surface 28 of the intramedullary nail 10.

FIGS. 4 and 5 depict a plurality of stabilizer members 22 disposed longitudinally in spaced relationship relates to each other along the longitudinal axis of the intramedullary nail 10 and radially relative to each other around the circumference of the intramedullary nail 10.

Figure 6:
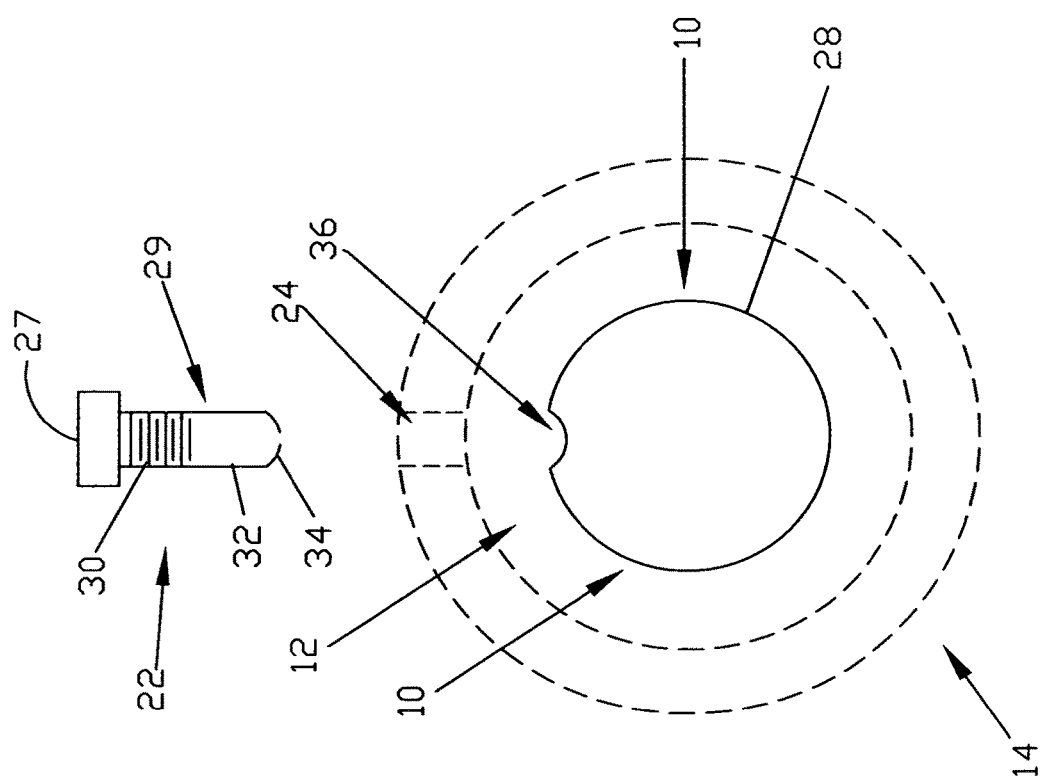
FIG. 6 is a top cross-sectional view of an intramedullary nail implanted in a fractured femur and a stabilizer member of the present invention before assembly.

As best shown in FIG. 6, each stabilizer member 22 comprises a head 27 having a shaft generally indicated as 29 extending outwardly therefrom including a proximal threaded shank portion 30 and a distal non-threaded shank portion 32 terminating in a blunt or convex tip or outer end 34. The outer surface 28 of the intramedullary nail 10 may include a seat 36 such as a dimple or recess to receive or engage the blunt or convex tip or outer end 34 of the stabilizer member 22 to prevent rotation of the intramedullary nail 10 about the longitudinal axis within the intramedullary canal 12. The length of the shaft 29 may be from about or substantially equal to the distance between the outer surface 28 of the intramedullary 10 to the inner surface of the cortex 26 or form about or substantially equal to the distance between the outer surface 28 of the intramedullary nail 10 and the outer surface of the cortex 26. As depicted, the stabilizer members 22 are disposed in spaced relationship relative to each other are around the circumference of intramedullary nail 10.

Figure 7:
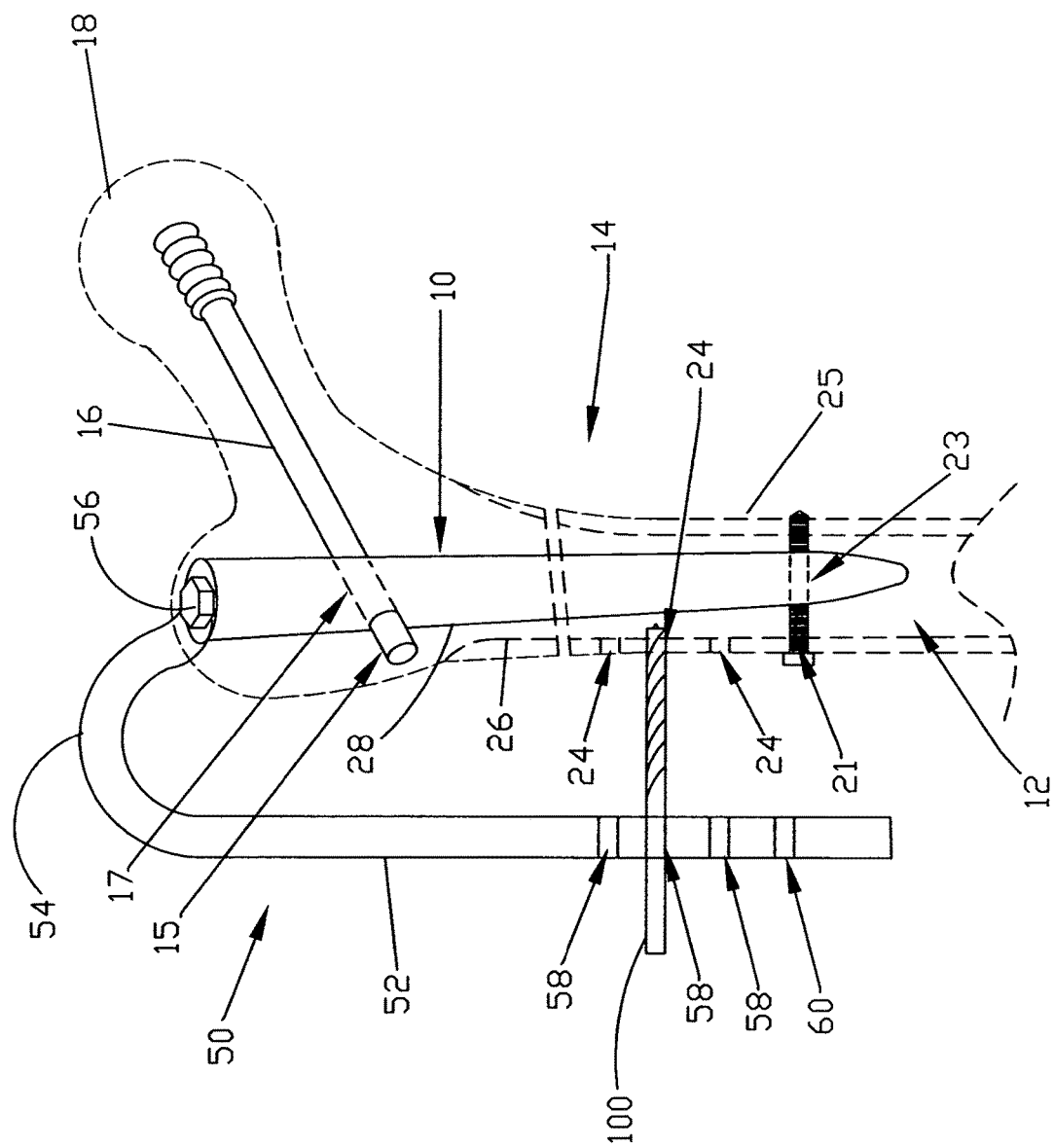
FIG. 7 is a view of an intramedullary nail implanted in a fractured femur having an alignment tool or jig of the present invention mounted thereon.
Figure 8:
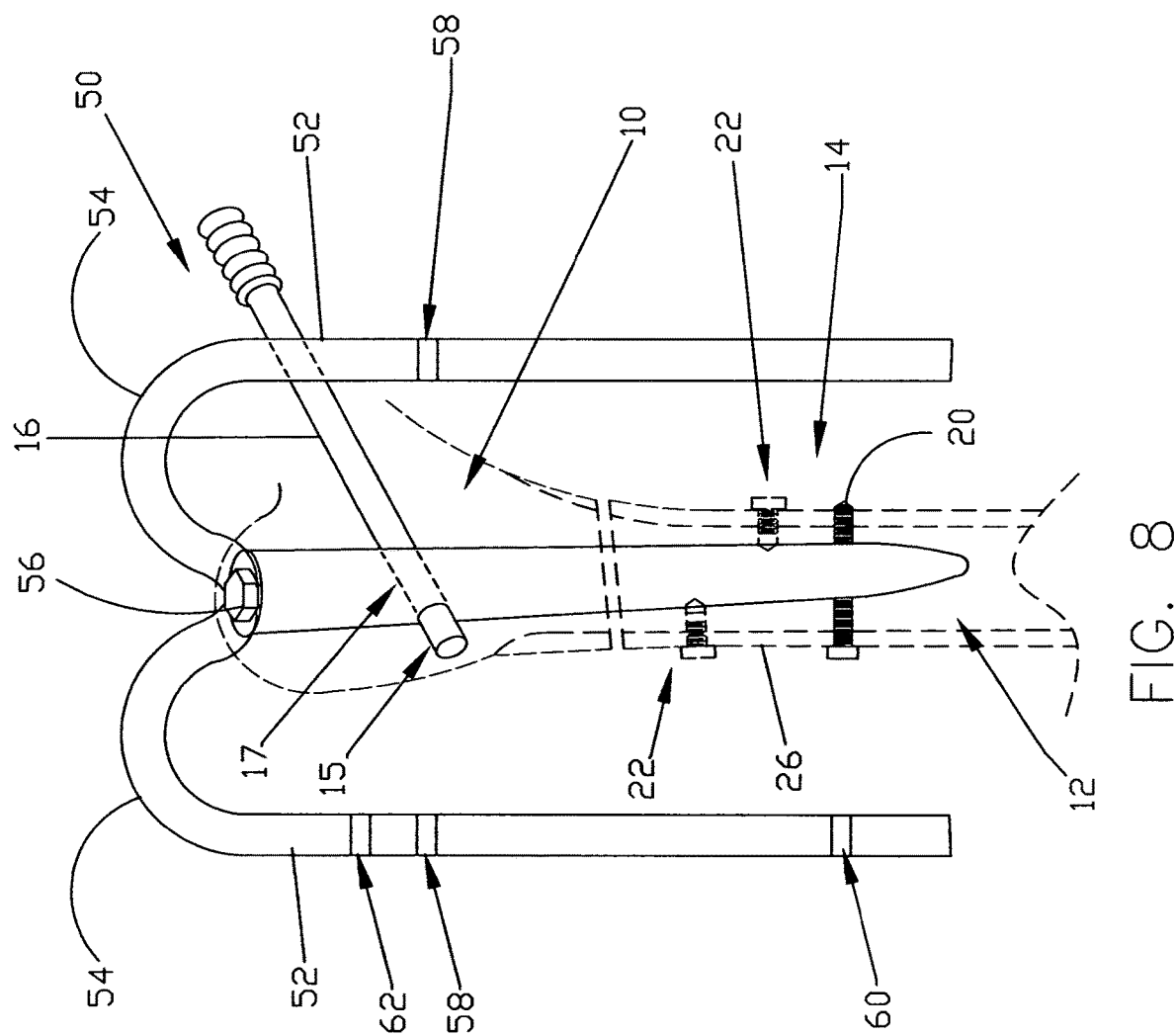
FIG. 8 is a view of an intramedullary nail implanted in a fractured femur having an alternate embodiment of an alignment tool or jig of the present invention mounted thereon.

An alignment tool generally indicated as 50 in FIGS. 7 and 8 is used to locate the correct positions or locations of the femur neck screw 16, stabilizer member(s) 22 and lower lock screw 20 along the intramedullary nail 10. The alignment tool comprises an alignment arm or member 52 removably coupled to or mounted on the upper portion of the intramedullary nail 10 by an intermediate coupling member 54. The alignment tool 50 may be removably secured to the intramedullary nail 10 by a 10 nut or screw 56 or other suitable fastener or coupling element to prevent rotation of the alignment tool 50 during the medical procedure. In use, the alignment arm or member 52 is substantially parallel to the intramedullary nail 10 when operatively coupled to or mounted thereon.

As shown in FIG. 7, the alignment arm or member 52 includes at least one 15 stabilizer alignment bore 58 and a locking screw alignment bore 60.

FIG. 8 depicts a similar alignment tool 50 having a pair of alignment arms or members each indicated as 52 including a plurality of stabilizer alignment bores each indicated as 58 and a locking screw alignment bore 60. In addition, a femur neck screw alignment bore 62 is formed in the upper portion of one of the alignment arms 20 or members 52.

The alignment bores 58, 60 and 62 provide for the proper relative longitudinal spacing of the femur neck screw 16, stabilizer member(s) 22 and locking screw 20 along the length of the intermedullary nail 10.

The upper or proximal portion of the intramedullary nail 10 may be secured in the medullary canal 12 prior to coupling or mounting the alignment tool 50 to the upper portion of the intramedullary nail 10 by drilling the channel 15 in the upper portion of the femur and the channel or hole 17 through the upper portion of the intramedullary nail 10 and into the head 18. The femur neck screw 16 is then threaded through the femur 14, the upper portion of the intramedullary nail 10 and into the head 18.

Alternately, the alignment tool 50 may be positioned on the intramedullary nail 10 disposed within the medullary channel 12 prior to securing the intramedullary nail 10 in the medullary canal 12 with the femur neck screw 16.

Figures 9, 9A, 9B:
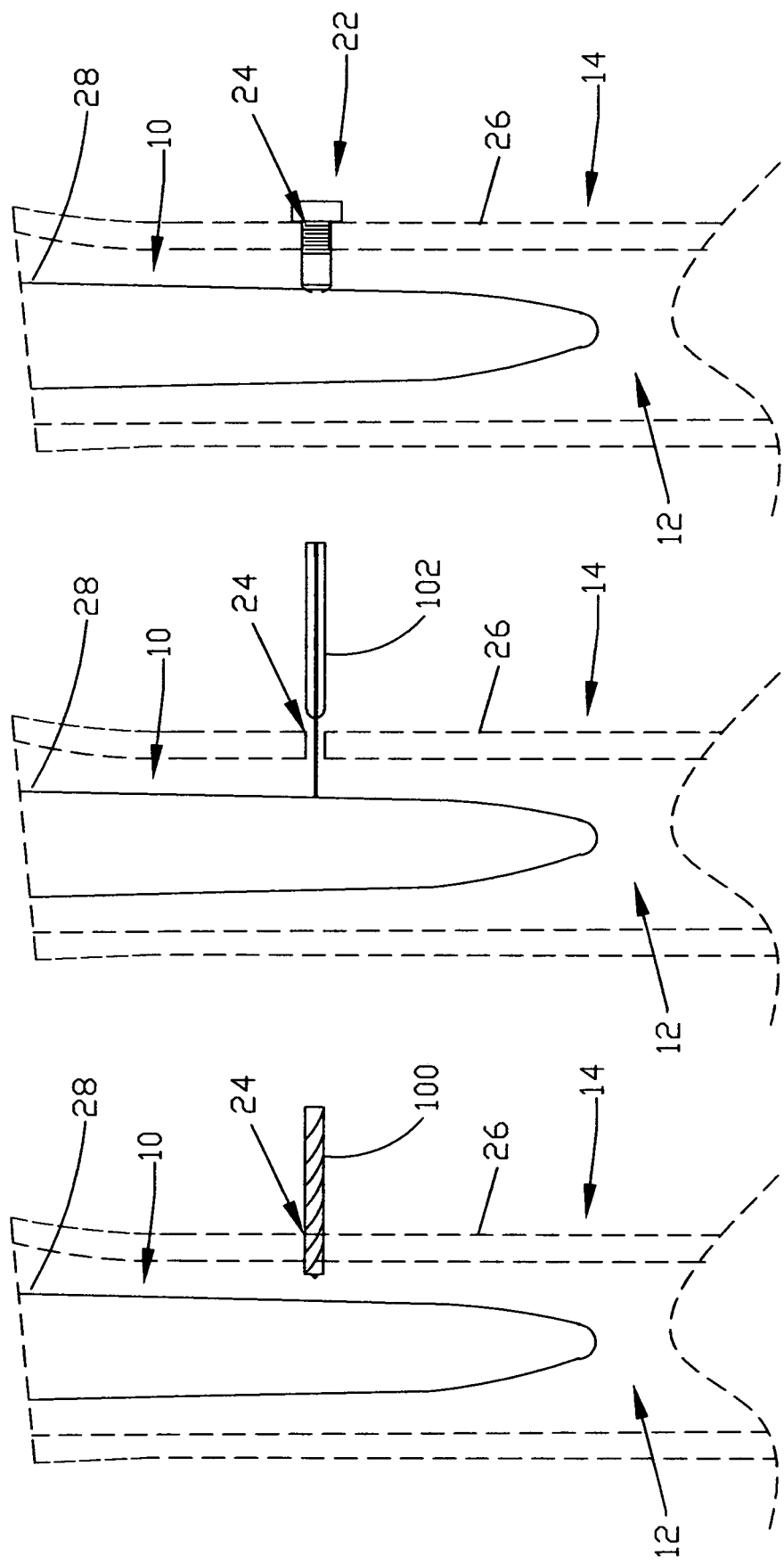
FIGS. 9, 9A and 9B show a partial view of an intramedullary nail implanted in a fractured femur depicting the steps of preparing the proximal cortex and positioning a stabilizer member of the present invention against the surface of the implanted intramedullary nail.

FIGS. 9, 9A and 9B show a drill bit 100 aligned with the intramedullary nail 10 through the stabilizer alignment bore 58 to drill through the proximal cortex 26 of the femur 14 to receive the stabilizer member(s) 22. Of course, alignment of the stabilizer member 22 is important when a dimple or recess 36 is formed in the surface of the intramedullary nail 10.

In similar fashion, the femur neck screw alignment bore 62 and the threaded locking screw alignment bore 60 are used to properly position a drill bit to drill or form the corresponding holes and channels to receive the femur neck screw 16 and locking screw 20 as shown in FIGS. 7 and 8.

The method of the present invention for securing and stabilizing the intramedullary nail 10 in the medullary canal 12 comprises the steps of:

preparing the medullary canal 12 to receive an intramedullary nail 10, positioning the intramedullary nail 10 in the medullary canal 12, securing the upper portion of the intramedullary nail 10 within the upper portion of the intramedullary canal 12 by a threading a femur neck screw 16 through the upper portion of femur 14 and channel or hole 17 formed through the intramedullary nail 10 and into the head 18, positioning an alignment tool 50 including a stabilizer member alignment bore 58 and a locking screw alignment bore 60 on the upper portion of the intramedullary nail 10, aligning a drill bit 100 through the locking screw alignment bore 60 and drilling a hole 21 through the proximal cortex 26 and a channel or hole 23 through distal portion of the intramedullary nail 10, securing the lower portion of the intramedullary nail 10 within the intramedullary canal 12 by threading a locking screw 20 through the hole 21 formed in proximal cortex 26 and the channel or hole 23 formed in the lower portion of the intramedullary nail 10 and into the distal cortex 25, aligning a drill bit 100 through the stabilizer member alignment bore 58 and drilling a hole 24 through the proximal cortex 26 of the femur 14, determining (measuring) the linear distance between the outer surface 19 of the proximal cortex 26 and the proximal surface 28 of the intramedullary nail 10 aligned with the stabilizer member alignment bore 58 with a measuring implement 102, selecting a stabilizer member 22 including a head 27 having a shaft 29 extending outwardly therefrom wherein the shaft 29 includes a proximal threaded shank portion 30 adjacent the head 27 and a distal unthreaded portion 32 having a blunt or convex end portion 34 wherein the length of the shaft 29 is substantially equal to the linear distance between the outer surface 19 of the proximal cortex 26 and the proximal surface 28 of the intramedullary nail 10 aligned with the stabilizer member alignment bore 58, inserting the stabilizer member 22 through the stabilizer alignment bore 58 and threading the stabilizer member 22 into the hole 24 until the end portion 34 of the distal non-shank portion 32 engages the proximal surface 28 of the intramedullary nail 10 and the proximal threaded shank portion 38 is threaded into the proximal cortex 26 adjacent the stabilizer alignment bore 58 to secure the stabilizer member 22 against the surface 28 of the intramedullary nail 10 to stabilize the intramedullary nail 10 from lateral movement, and removing the alignment tool 50 from the upper end portion of the intramedullary nail 10.

As shown in FIGS. 4 and 5, multiple stabilizers members 22 may be used to further enhance lateral stability of the intramedullary nail 10 and to prevent rotation of the intramedullary nail 10.

In an alternate embodiment, the method of securing and stabilizing the intramedullary nail 10 to be implanted in the medullary canal 12 comprises the steps of:

preparing the medullary canal 12 to receive an intramedullary nail 10, positioning the intramedullary nail 10 in the medullary canal 12, positioning an alignment tool 50 including a femur neck screw alignment bore 62, a stabilizer member alignment bore 58 and a locking screw alignment bore 60 on the upper or proximal end portion of the intramedullary nail 10, aligning a drill bit through the femur neck screw alignment bore 62 and drilling a channel 15 in the femur 14 and a channel or hole 17 through the upper or proximal portion of the intramedullary nail 10 and into the head 18, securing the upper portion of the intramedullary nail 10 within the upper portion of the intramedullary canal 12 by threading a femur neck screw 16 through channel 15 and channel or hole 17 and into the head 18, aligning a drill bit 100 through the locking screw alignment bore 60 and drilling a hole 21 through the proximal cortex 26 and a channel or hole 23 through the distal portion of the intramedullary nail 10, securing the lower portion of the intramedullary nail 10 within the intramedullary canal 12 by threading a locking screw 20 through the hole 21 formed in proximal cortex 26 and through the channel or hole 23 formed in the lower portion of the intramedullary nail 10 and into the distal cortex 25, aligning a drill bit 100 through the stabilizer member alignment bore 58 and drilling a hole 24 through the proximal cortex 26 of the femur 14, determining (measuring) the linear distance between the outer surface 19 of the proximal cortex 26 and the proximal surface 28 of the intramedullary nail 10 aligned with the stabilizer member alignment bore 58 with a measuring implement 102, selecting a stabilizer member 22 including a head 27 having a shaft 29 extending outwardly therefrom wherein the shaft 29 includes a proximal threaded shank portion 30 adjacent the head 27 and a distal unthreaded portion 32 having a blunt or convex end portion 34 wherein the length of the shaft 29 is substantially equal to the linear distance between the outer surface 19 of the proximal cortex 26 and the proximal surface 28 of the intramedullary nail 10 aligned with the stabilizer member alignment bore 58, inserting the stabilizer member 22 through the stabilizer alignment bore 58 and threading the stabilizer member 22 into the hole 24 until end portion 34 of the distal non-shank portion 32 engages the proximal surface 28 of the intramedullary nail 10 and the proximal threaded shank portion 38 is threaded into the proximal cortex 26 adjacent the stabilizer alignment bore 58 to secure the stabilizer member 22 against the surface 28 of the intramedullary nail 10 to stabilize the intramedullary nail 10 from lateral movement, and removing the alignment tool 50 from the upper end portion of the intramedullary nail 10.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

In describing the invention, certain terms are used for brevity, clarity, and understanding. No unnecessary limitations should be inferred beyond the requirement of the prior art because such terms are used for descriptive purposes and are intended to be broadly construed. The different structural and functional elements, apparatuses, devices, compositions, and methods described herein may be used alone or in combination with other structural and functional elements, apparatuses, devices, compositions, systems and methods. It is to be expected that various equivalents, alternatives and modifications are possible within the scope of the claims hereinafter.

What is claimed is:

1. A method for securing and stabilizing an intramedullary nail in a medullary canal comprising the steps of:
    preparing the medullary canal having an upper portion and a lower portion to receive the intramedullary nail including an upper portion and a lower portion,
    positioning the intramedullary nail in the medullary canal,
    securing the upper portion of the intramedullary nail within the upper portion of the intramedullary canal by threading a femur neck screw through the upper portion of a femur having a proximal cortex and a distal cortex and a channel or hole formed through the intramedullary nail and into a femur head,
    positioning an alignment tool including at least two stabilizer member alignment bores and a locking screw alignment bore on the upper portion of the intramedullary nail,
    aligning a drill bit through the locking screw alignment bore and drilling a hole through the proximal cortex and a channel through the lower portion of the intramedullary nail,
    securing the lower portion of the intramedullary nail within the medullary canal by threading a locking screw through the hole formed in the proximal cortex and the channel formed in the lower portion of the intramedullary nail and into the distal cortex of the femur,
    aligning a drill bit through each stabilizer member alignment bore and drilling a corresponding hole through the proximal cortex of the femur,
    selecting at least two stabilizer members each including a head having a central shaft extending outwardly therefrom wherein said central shaft includes a proximal threaded shank portion and a distal non-threaded shank portion,
    inserting said central shaft of the each stabilizer member through a corresponding stabilizer alignment bore such that the stabilizer members are disposed apart in a spaced relationship around a circumference of the intramedullary nail and threading said proximal threaded shank portion of the central shaft of each said stabilizer member into the proximal cortex until said distal non-threaded shank portion of said central shaft of said stabilizer member engages a corresponding dimple formed in the circumference of the intramedullary nail and adjacent the corresponding stabilizer alignment bore to secure each said stabilizer member against the circumference of the intramedullary nail to stabilize the intramedullary nail from movement,
    and removing the alignment tool from the upper portion of the intramedullary nail.

2. The method of claim 1 further comprising the step of measuring the linear distance between the outer surface of the PROXIMAL cortex and the surface of the intramedullary nail aligned with each stabilizer member alignment bore with a measuring implement and selecting a stabilizer member having a shaft with a length equal to the linear distance between the outer surface of the proximal cortex and the surface of the intramedullary nail aligned with the corresponding stabilizer member alignment bore.

3. The method of claim 1 wherein said distal non-threaded shank portion terminates in a convex tip.

4. A method for securing and stabilizing an intramedullary nail including an upper portion and a lower portion and including a circumference in a medullary canal including an upper portion and a lower portion of a fractured femur including a proximal cortex and a distal cortex and having an upper portion and a lower portion and a femur head comprises the steps of:
    preparing the medullary canal to receive the intramedullary nail,
    positioning the intramedullary nail in the medullary canal,
    positioning an alignment tool including a femur neck screw alignment bore, at least two stabilizer alignment bores and a locking screw alignment bore on the upper portion of the intramedullary nail;

aligning a drill bit through the femur neck screw alignment bore and drilling a channel in the femur and a channel or hole through the intramedullary nail and into the femur head;

securing the upper portion of the intramedullary nail within the upper portion of the medullary canal by a threading a femur neck screw through the channel formed in the femur and the channel or hole formed through the intramedullary nail and into the femur head, aligning a drill bit through the locking screw alignment bore and drilling a hole through the proximal femur cortex and a channel or hole through the lower portion of the intramedullary nail, securing the lower portion of the intramedullary nail within the medullary canal by threading a locking screw through the hole formed in the proximal femur cortex and the channel or hole formed in the lower portion of the intramedullary nail and into the distal femur cortex, aligning a drill bit through said at least two stabilizer member alignment bores and drilling a corresponding hole through the proximal femur cortex, selecting at least two stabilizer members each including a head having a central shaft extending outwardly therefrom wherein said entire shaft includes a proximal threaded shank portion and a distal non-threaded shank portion, inserting said central shaft of each said stabilizer member through the corresponding stabilizer alignment bore such that the stabilizer members are disposed apart in a spaced relationship around the circumference of the intramedullary nail and threading the proximal threaded shank portion of said central shaft of each said stabilizer member into the femur cortex until the distal non-threaded shank portion of said central shaft of each said stabilizer member engages a corresponding dimple formed in the circumference of the intramedullary nail adjacent said corresponding stabilizer alignment bore to secure each said stabilizer member against the circumference of the intramedullary nail to stabilize the intramedullary nail from movement, and removing the alignment tool from the upper portion of the intramedullary nail.

5. The method of claim 4 further comprising the step of measuring the linear distance between the outer surface of the proximal cortex and the surface of the intramedullary nail aligned with each stabilizer member alignment bore with a measuring implement and selecting stabilizer members having a shaft with a length equal to the linear distance between the outer surface of the proximal cortex and the surface of the intramedullary nail aligned with each corresponding stabilizer member alignment bore.

* * * * *